(12) United States Patent
Lee et al.

(10) Patent No.: US 7,834,203 B2
(45) Date of Patent: Nov. 16, 2010

(54) MANUFACTURING METHOD OF BIO-DIESEL OIL

(75) Inventors: Jin-Suk Lee, Daijeon (KR); Deog-Keun Kim, Daejeon (KR); Soon-Chul Park, Seoul (KR); Joon-Pyo Lee, Daejeon (KR); Sung-Hyun Kim, Daejeon (KR); Keun-Hoo Lee, Seoul (KR)

(73) Assignee: Korea Institute of Energy Research, Daejeon (KR)

( * ) Notice: Subject to any disclaimer, the term of this patent is extended or adjusted under 35 U.S.C. 154(b) by 748 days.

(21) Appl. No.: 10/551,364

(22) PCT Filed: Mar. 8, 2004

(86) PCT No.: PCT/KR2004/000483

§ 371 (c)(1),
(2), (4) Date: Feb. 27, 2006

(87) PCT Pub. No.: WO2004/085585

PCT Pub. Date: Oct. 7, 2004

(65) Prior Publication Data

US 2006/0293532 A1    Dec. 28, 2006

(30) Foreign Application Priority Data

Mar. 28, 2003    (KR) .................. 10-2003-0019649

(51) Int. Cl.
*C11C 3/00*    (2006.01)
*C10L 1/18*    (2006.01)

(52) U.S. Cl. .................. 554/169; 554/167; 554/170; 554/174; 44/308; 44/385; 44/388

(58) Field of Classification Search .................. 554/167, 554/169, 170, 174; 44/308, 385, 388
See application file for complete search history.

(56) References Cited

U.S. PATENT DOCUMENTS 4,608,202 A    8/1986    Lepper et al.

(Continued)

FOREIGN PATENT DOCUMENTS

AT    386222 B    7/1988

(Continued)

OTHER PUBLICATIONS

Peterson et al., Rapseed Oil Transestrification by Heterogeneous Catalysis, 1984, JAOCS, vol. 61, No. 10, pp. 1593-1597.*

(Continued)

*Primary Examiner*—Porfirio Nazario Gonzalez
*Assistant Examiner*—Yate' K Cutliff
(74) *Attorney, Agent, or Firm*—TIPS Group

(57) ABSTRACT

The object of this invention is to provide a method of producing a bio-diesel oil in a great amount in a relatively short time, in which oil/fat and alcohol, used as reactants, are homogeneously mixed with each other to form a single liquid phase mixture which effectively react with each other. The method includes transesterifying the oil/fat and alcohol in the presence of alkyl ester. Additionally, in the method, alkyl ester is added to a mixture of the oil/fat and alcohol by recycling alkyl ester as a product to the mixture. Furthermore, the method includes (a) an acidic catalyst, and (b) transesterifying the pre-esterified oil/fat with alcohol in the presence of alkyl ester.

10 Claims, 8 Drawing Sheets

U.S. PATENT DOCUMENTS

| | | | |
|---|---|---|---|
| 5,116,546 A | | 5/1992 | Klok et al. |
| 5,354,878 A | | 10/1994 | Connemann et al. |
| 5,514,820 A | | 5/1996 | Assmann et al. |
| 5,939,571 A | * | 8/1999 | Foidl .......................... 554/12 |
| 6,933,398 B2 | * | 8/2005 | Peter et al. .................. 554/169 |

FOREIGN PATENT DOCUMENTS

| | | | |
|---|---|---|---|
| AT | 394 374 B | | 3/1992 |
| CA | 2131654 | | 3/1996 |
| EP | 0127104 A1 | | 12/1984 |
| EP | 0523767 A2 | | 1/1993 |
| EP | 0535290 A1 | | 4/1993 |
| EP | 0562504 A2 | | 9/1993 |
| GB | 612667 | * | 11/1948 |
| GB | 612667 A | | 11/1948 |
| KR | 10-1999-024530 | | 4/1999 |
| WO | WO 93/09212 | | 5/1993 |
| WO | WO 95/02661 | | 1/1995 |
| WO | WO 97/00234 | | 1/1997 |
| WO | WO 9700234 A1 | * | 1/1997 |
| WO | WO 99/26913 | | 6/1999 |
| WO | WO 03/004591 A1 | * | 1/2003 |
| WO | PCT/KR2004/000483 | | 8/2004 |

OTHER PUBLICATIONS

Peter, S. et al., Method for Transesterification of fats and/or oils by means of alcoholysis, Jan. 16, 2003, WO 03/004591 (A1), English language translation, 5 pages.*

* cited by examiner

MANUFACTURING METHOD OF BIO-DIESEL OIL

TECHNICAL FIELD

The present invention pertains, in general, to a method of transesterifying oil/fat with alcohol to produce a bio-diesel oil and, more particularly, to a method of transes-terifying oil/fat with alcohol to produce a bio-diesel oil, in which when the oil/fat and alcohol are transesterified with each other, alkyl ester is added to two reactants immiscible with each other to promote the homogeneous mixing of the two reactants to form a sigle liquid phase, thereby producing a great amount of bio-diesel oil in a relatively short time in comparison with a conventional method of producing the bio-diesel oil.

BACKGROUND ART

Generally, the advance in industrialization is accompanied by the increase in the production of industrial machines including diesel engines and automobiles, increasing the consumption of a diesel oil used as a fuel of the industrial machines and automobiles. Of various fuels produced from crude oil, diesel oil is competitive because of its relatively low cost, but is problematic in that combustion using diesel oil as fuel causes greater pollution than other kinds of fuels.

Much effort has been made to develop a bio-diesel oil as a substitute fuel having similar physical properties to the diesel oil and capable of preventing air pollution in order to overcome such a problem experienced with combustion using the diesel oil.

The bio-diesel oil is an esterified oil produced by reacting a regenerable oil/fat, such as vegetable oil, animal fat, and waste frying oil with alcohol in the presence or absence of a catalyst. Having similar physical properties to light oil used as the fuel for the diesel engines, the bio-diesel oil may be used with light oil, or used alone without using light oil in the diesel engines.

It is necessary to understand some production characteristics of the bio-diesel oil in order to develop a process for effectively producing the bio-diesel oil. Firstly, the production of the bio-diesel oil is characterized in that the bio-diesel oil is produced through a reversible reaction. Accordingly, a batch reactor or a plug flow reactor (PFR) maintaining high concentrations of reactants therein is more preferable than a continuous stirred tank reactor (CSTR) maintaining low concentrations of the reactants therein when it is required to maintain a high reaction rate.

Secondly, polar alcohol is used to produce the bio-diesel oil (various alcohols may be used to produce the bio-diesel oil, but relatively low-priced methanol is most frequently used to practically produce the bio-diesel oil). As described above, alcohol used as one of the reactants is polar liquid, but the oil/fat used as the other reactant is non-polar liquid. Therefore, the two reactants are immiscible with each other, but exist in two separate phases. At this time, the reaction between the two reactants is conducted at only an interface between the two reactants, thereby reducing the reaction rate of the oil/fat and alcohol.

Thirdly, it is preferable that a continuous reactor be used instead of the batch reactor to produce the bio-diesel oil because the bio-diesel oil must be produced as fuel for automobiles in a great amount. Hence, the PFR or CSTR is preferable in comparison with the batch reactor. Taking all the above into consideration, it can be seen that it is necessary to use the PFR to produce the bio-diesel oil in a great amount, and to homogeneously mix the oil/fat with alcohol to increase the reaction rate of alcohol with the oil/fat.

The homogeneous mixing of the oil/fat and alcohol has been developed in the art, as indicated by U.S. Pat. No. 5,514,820, which discloses a two-step continuous process of producing low alkyl ester using alcohol and oil/fat in the presence of a liquid catalyst. According to this patent ('820), the pre-heated oil/fat reacts with alcohol in the presence of a catalyst solution in a plug flow reactor to produce glycerine and ester, and glycerine thus produced is separated from ester in the first step. In the second step, alcohol reacts again with the oil/fat in the catalyst solution in the plug flow reactor to produce ester and glycerine, and glycerine is separated from ester to produce low alkyl ester.

In this respect, because alcohol is immiscible with the oil/fat, it is required to maintain a Reynolds number to be 10,000 or higher so as to enable a mixture of alcohol and oil/fat to flow in a form of a turbulent flow instead of a laminar flow through the reactor to increase the reaction rate of alcohol with oil/fat. However, a length of the plug flow reactor must be sufficiently long, or a flow rate of the mixture of alcohol and oil/fat must be desirably high in order to enable the mixture to flow in the form of the turbulent flow through the plug flow reactor causing the enlargement in volume of the reactor and the increase in power costs, thereby undesirably increasing the production costs of low alkyl ester. In addition, the above patent is problematic in that a separation time of glycerine from alkyl ester is undesirably long because liquid drops of the product are finely broken during a settling process of separating glycerine from alkyl ester.

Furthermore, Canadian Pat. Laid-Open Publication No. 2,131,654 (Mar. 9,1996) recites a process of reacting fatty acid glyceride with alcohol in the presence of a catalyst using a subsidiary solvent to produce low alkyl fatty acid ester.

According to the patent ('654), fatty acid glyceride and alcohol are immiscible with each other if they are mixed with each other without sufficient agitation. Hence, in the case of the reaction of alcohol and fatty acid glyceride without sufficient agitation, the contact area between alcohol and fatty acid glyceride is relatively small, and the reaction rate is relatively slow because the reaction of alcohol and fatty acid glyceride is achieved at only an interface between them. In the above patent ('654), the subsidiary solvent, such as tetrahydrofuran (THF) and 1,4-dioxane, is added to reactants so as to increase the contact area between alcohol and fatty acid glyceride to increase the reaction rate, thereby leading to a homogeneous liquid mixture of alcohol and fatty acid glyceride to quickly convert the two phases into a single phase to sufficiently increase the reaction rate even though the reactants are in a laminar flow region with a low agitation speed. However, the patent ('654) has a disadvantage in that the subsidiary solvent must be separated from the product after the completion of the reaction of fatty acid glyceride with alcohol leading to the additional costs of installation and operation of a subsidiary solvent separating device, thereby ensuring low economic efficiency.

Meanwhile, Austrian Pat. Laid-Open Publication No. PCT/AT 98/00284 (International Publication No. WO 99/26913) discloses a method and a device for producing fatty acid methyl ester.

In this respect, an interface area between reactants is enlarged due to a high energy turbulent flow or a dynamic turbulent flow. However, the above Austrian patent is disadvantageous in that the enlarged interface area is obtained by use of an additional agitator, which also has the same disadvantages as the patents described above.

DISCLOSURE OF INVENTION

Technical Problem

Accordingly, the present invention has been made keeping in mind the above problems occurring in the prior art, and an object of the present invention is to provide a method of producing a bio-diesel oil in a great amount in a relatively short time, in which an oil/fat and alcohol immiscible with each other are transesterified to be quickly converted into a single phase mixture by using a fatty acid alkyl ester product as a subsidiary solvent, thereby promoting the reaction of the oil/fat and alcohol.

Another object of the present invention is to provide a method of producing a bio-diesel oil in a great amount in a relatively short time, in which a portion of fatty acid alkyl ester (hereinafter, referred to as 'alkyl ester') as a product is recycled to reactants during a transesterification reaction of an oil/fat with alcohol to act as a subsidiary solvent to quickly convert the reactants immiscible with each other into a single phase mixture, thereby promoting the reaction of the oil/fat and alcohol.

A further object of the present invention is to provide a method of producing a bio-diesel oil, further including pre-esterification step of oil/fat with alcohol so as to convert free fatty acids contained in an oil/fat used as a reactant into the bio-diesel oil to improve reaction efficiency of a transesterification reaction of the oil/fat and alcohol.

Yet another object of the present invention is to provide a method of producing a bio-diesel oil in a great amount in a relatively short time through a relatively small reaction system using a batch-type reactor or a continuous-type reactor.

Technical Solution

In order to accomplish the above object, according to the first aspect of the present invention, there is provided a method of transesterifying an oil/fat with alcohol in the presence of alkyl ester to produce a bio-diesel oil. At this time, alkyl ester is added to the oil/fat and alcohol from an early stage of a transesterification reaction.

According to the second aspect of the present invention, there is provided a method of producing the bio-diesel oil, in which alkyl ester is added to a mixture of the oil/fat and alcohol by recycling alkyl ester as a product to the mixture.

At this time, alkyl ester is added to the oil/fat and alcohol in an amount of 1 to 30% based on the weight of the oil/fat.

The oil/fat is selected from the group consisting of vegetable oil/fat, animal oil/fat, waste frying oil, regenerated oil/fat, and a mixture thereof.

Preferably, the alcohol is selected from the group consisting of $C_1$ to $C_{10}$ alcohols, and a mixture thereof.

Additionally, the oil/fat reacts with the alcohol in a molar ratio of 1:3 to 1:12.

It is preferable that the oil/fat react with the alcohol in the presence of a basic catalyst or an acidic catalyst.

When the basic catalyst or the acidic catalyst is a homogeneous catalyst, the basic catalyst or the acidic catalyst is added to the oil/fat and alcohol in an amount of 0.3 to 2.0% based on the weight of the oil/fat.

On the other hand, when the basic catalyst or the acidic catalyst is a heterogeneous catalyst, the basic catalyst or the acidic catalyst is added to the oil/fat and alcohol in an amount of 5 to 80% based on the volume of a reactor.

Further, the oil/fat reacts with alcohol in a batch reactor, a plug flow reactor, or a continuous stirred tank reactor. When a plurality of reactors are used to react the oil/fat with the alcohol, the reactors are arranged in series, in parallel, or in combination of series and parallel.

According to the third aspect of the present invention, there is provided a method of producing a bio-diesel oil, including (a) pre-esterifying free fatty acids, contained in an oil/fat, with alcohol in the presence of an acidic catalyst, and (b) transesterifying the pre-esterified oil/fat and alcohol in the presence of alkyl ester.

At this time, the step (a) further includes adding alkyl ester as a product to the reactants.

In addition, a portion of the product comprising the alkyl ester produced by step (b) is directly recycled to the reaction mixture of step (a) and/or step (b) prior to separating the alkyl ester and glycerine in a separator.

Furthermore, alkyl ester of the step (a) or/and the step (b) is added to the reactants in an amount of 1 to 30% based on the weight of the oil/fat.

As well, the oil/fat of the step (a) is selected from the group consisting of vegetable oil/fat, animal oil/fat, waste frying oil, and regenerated oil/fat, which contains the free fatty acid.

Moreover, alcohol of the step (a) and the step (b) is selected from the group consisting of $C_1$ to $C_{10}$ alcohols, and a mixture thereof.

The oil/fat containing the free fatty acid reacts with the alcohol in a molar ratio (Oil/fat:alcohol) of 1:0.3 to 1:3 in the step (a), and the oil/fat reacts with the alcohol in a molar ratio of 1:3 to 1:12 in the step (b).

Additionally, the step (a) is conducted in the presence of the acidic catalyst, and the step (b) is conducted in the presence of the basic catalyst or the acidic catalyst.

When the basic catalyst or acidic catalyst is a heterogeneous catalyst, the basic catalyst or acidic catalyst is added to reactants in an amount of 5 to 80% based on the volume of a reactor. On the other hand, when the basic catalyst or acidic catalyst is a homogeneous catalyst, the basic catalyst or acidic catalyst is added to the reactants in an amount of 0.3 to 2.0% based on the weight of an oil/fat.

As well, the oil/fat reacts with alcohol in a batch reactor, a plug flow reactor, or a continuous stirred tank reactor. When a plurality of reactors are used to react the oil/fat with the alcohol, the reactors are arranged in series, in parallel, or in combination of series and parallel.

DESCRIPTION OF DRAWINGS

The above and other objects, features and other advantages of the present invention will be more clearly understood from the following detailed description taken in conjunction with the accompanying drawings, in which.

BEST MODE

Figure 1:
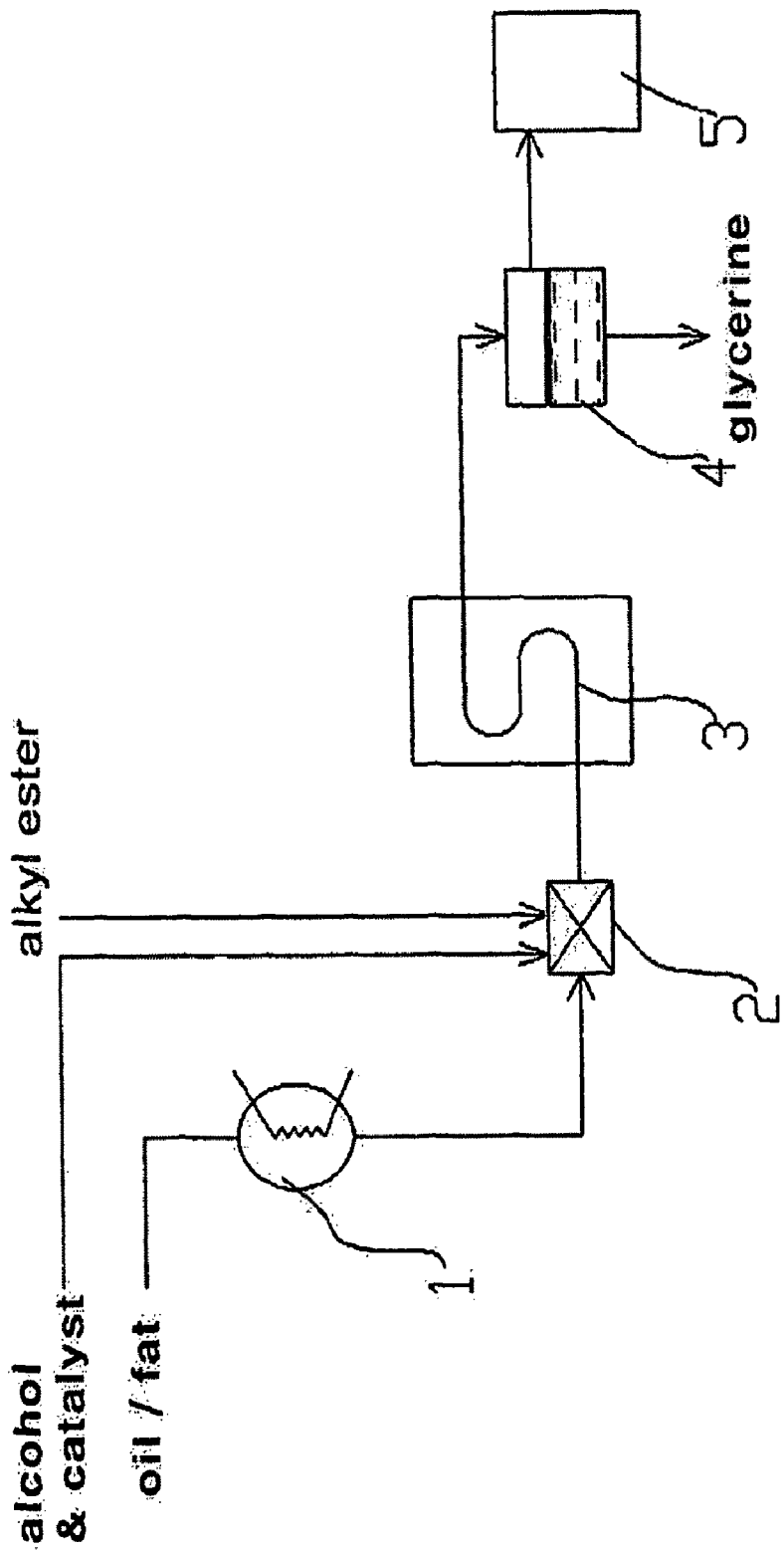
FIG. 1 illustrates the production of a bio-diesel oil using a PFR according to the first aspect of the present invention.

Reference should now be made to the drawings, in which the same reference numerals are used throughout the different drawings to designate the same or similar components.

According to the present invention, there is provided a method of producing a bio-diesel oil in a great amount in a relatively short time through a relatively small reaction system, in which an oil/fat and alcohol used as reactants are homogeneously mixed with each other to form a single phase liquid mixture. At this time, a reaction rate of the reactants must be fast in order to produce a desired product, and the reactants must be homogeneously mixed with each other to form the single phase mixture so as to increase the reaction rate. However, traditionally, the oil/fat is immiscible with alcohol because the oil/fat is a non-polar liquid and alcohol is a polar liquid.

In the present invention, alkyl ester is used to make the reactants with different polarities into a single liquid phase mixture. That is to say, use of alkyl ester in the production of the bio-diesel oil leads to the homogeneous mixing of the oil/fat and alcohol used as the reactants, thereby accelerating the reaction rate of the oil/at and alcohol.

Alkyl ester, useful in the present invention may be any material capable of homo-geneously mixing the non-polar oil/fat with polar alcohol to form the single liquid phase mixture, is preferably derived from a fatty acid, and has a structure of the following Formula 1.

$R_1COOR$         Formula 1.

wherein, R is preferably $C_1$ to $C_{10}$ alkyl groups, and more preferably selected from the group consisting of a methyl group, an ethyl group, a propyl group, a butyl group, a pentyl group, and isomers thereof (structural isomers, stereo-isomers, and the like). $R_1$ is an alkyl group, and preferably the alkyl group in which the number of carbons is properly controlled such that the number of carbons of alkyl ester having the Formula 1 structure is 10 to 24.

A preferable compound of the Formula 1 is exemplified by methyl ester ($R_1COOCH_3$), ethyl ester ($R_1COOC_2H_5$), propyl ester ($R_1COOC_3H_7$), butyl ester ($R_1COOC_4H_9$), and pentyl ester ($R_1COOC_5H_{11}$).

In this regard, commercial alkyl ester may be added to the reactants, or a portion of alkyl ester produced according to the following Reaction equation 1 may be recycled to the reactants. The latter is more preferable than the former in consideration of the costs of the reactants.

Reaction equation 1

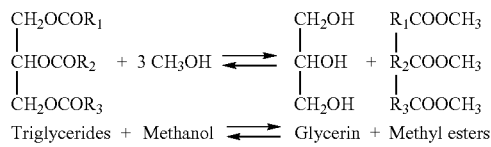

$$\begin{array}{c}CH_2OCOR_1\\CHOCOR_2\\CH_2OCOR_3\end{array} + 3\,CH_3OH \rightleftharpoons \begin{array}{c}CH_2OH\\CHOH\\CH_2OH\end{array} + \begin{array}{c}R_1COOCH_3\\R_2COOCH_3\\R_3COOCH_3\end{array}$$

Triglycerides + Methanol $\rightleftharpoons$ Glycerin + Methyl esters wherein, R is preferably $C_1$ to $C_{10}$ alkyl groups, and more preferably selected from the group consisting of a methyl group, an ethyl group, a propyl group, a butyl group, a pentyl group, and isomers thereof (structural isomers, stereo-isomers, and the like). $R_1$, $R_2$, and $R_3$ each are an alkyl group, and preferably the alkyl group in which the number of carbons is properly controlled such that the number of carbons of alkyl ester, as the product obtained according to the Reaction equation 1, is 10 to 24. At this time, $R_1$, $R_2$, and $R_3$ may or may not be the same as each other.

The oil/fat used as the reactant may be selected from the group consisting of vegetable oil/fat, animal oil/fat, waste frying oil, regenerated oil/fat, and a mixture thereof.

The vegetable oil/fat is exemplified by soybean oil, corn oil, rape oil, linseed oil, sunflower oil, poppy-seed oil, walnut oil, peanut oil, cottonseed oil, rice bran oil, camellia oil, castor oil, and olive oil. Additionally, examples of animal oil/fat include beef tallow, lard, sheep oil, fish oil, and whale-oil.

Any alcohol may be used as the reactant so long as it is applied to a transesterification reaction. For example, alcohol is preferably $C_1$ to $C_{10}$ alcohols, and selected from the group consisting of methyl alcohol, ethyl alcohol, propyl alcohol, butyl alcohol, and pentyl alcohol. It is most preferable to use methyl alcohol as the reactant in relation to yield and economic efficiency.

As described above, the oil/fat and alcohol, used as the reactants and immiscible with each other, are converted to a liquid single phase mixture in the presence of alkyl ester, and then subjected to an esterification reaction. A non-limiting, illustrative molar ratio of oil/fat and alcohol is preferably 1:3 to 1:12. At this time, alkyl ester is preferably added to the reactants in an amount of 1 to 30% based on the weight of the oil/fat.

The transesterification of the oil/fat with alcohol may be conducted at 40 to 120° C. for 0.05 to 2 hours according to the kind of reactant.

Additionally, the transesterification is preferably conducted in the presence of the catalyst. In this respect, an acidic catalyst or a basic catalyst may be used in the transesterification.

Examples of the acidic catalyst include a liquid sulfuric acid catalyst as a homogeneous catalyst, and a solid acidic catalyst, such as a strong acidic ion exchange resin and sulfate zirconia, as a heterogeneous catalyst.

The basic catalyst is exemplified by potassium hydroxide, sodium hydroxide, and sodium methylate as the homogeneous catalyst, and a solid basic catalyst as the heterogeneous catalyst. Examples of the solid basic catalyst include Na/NaOH/γ-$Al_2O_3$, $Cs_xO$/γ-$Al_2O_3$ (x is preferably 0.1 to 2).

The acidic catalyst has a disadvantage in that it must be used under relatively high temperature and pressure in comparison with the basic catalyst. But, the acidic catalyst is useful in the case of using the oil/fat containing a free fatty acid in relative abundance even though it has the above disadvantage.

Currently, the basic catalyst is more frequently used than the acidic catalyst because the basic catalyst is used in a relatively moderate reaction condition in comparison with the acidic catalyst. However, the basic catalyst should not be used in the case of using the oil/fat plentifully containing the free fatty acid as the reactant. In other words, because the free fatty acid contained in the oil/fat forms a salt (soap) in the presence of the basic catalyst through a neutralization reaction, activity of the basic catalyst is reduced and the consumption of the basic catalyst is increased when the oil/fat plentifully contains the free fatty acid, thereby reducing economic efficiency of the production of the bio-diesel oil (refer to Table 1—Comparison of sulfuric acid as the acidic catalyst with potassium hydroxide as the basic catalyst).

TABLE 1

|  | Acidic catalyst (sulfuric acid) | Basic catalyst (KOH) |
|---|---|---|
| Operation Pressure | Max. 80 atm | Max. 9 atm |
| Operation Temperature | Max. 250° C. | Max. 100° C. (average: 60 to 80° C.) |
| Reaction Time | 2 to 4 hours | 0.1 to 0.2 hours |
| Characteristics | Applied to a raw material containing a high free fatty acid content (2% or more) | Applied to a raw material containing a law free fatty acid content (0.5% or more) |

A detailed description will be given later of a pre-esterification process to overcome the above disadvantages occurring in use of the basic catalyst.

When the oil/fat has a free fatty acid content of 2% or more, the acidic catalyst is more preferable than the basic catalyst. On the other hand, when the oil/fat has a free fatty acid content of 0.5% or less, the basic catalyst is more preferable than the acidic catalyst.

The amount of the acidic catalyst or the basic catalyst added to the reactants is not limited as long as the acidic catalyst or the basic catalyst is added to the reactants in a sufficient amount so as to activate the transesterification reaction. In detail, in the case of using the homogeneous catalyst, the amount of the catalyst added to the reactants is preferably 0.3 to 2.0% based on the weight of the oil/fat. On the other hand, in the case of using the solid acidic catalyst or the solid basic catalyst as the heterogeneous catalyst, the amount of the catalyst added to the reactants is preferably 5 to 80% based on the volume of a packed column used in the transesterification reaction. Additionally, in the case of using a batch reactor or a continuous stirred tank reactor, the amount of the catalyst is preferably 5 to 40% in consideration of the agitation characteristics and physical properties of the catalyst.

The transesterification according to the present invention is conducted using the batch reactor, or the continuous reactor, such as the plug flow reactor, and the continuous stirred tank reactor. When a plurality of reactors are used to conduct the transesterification, the reactors may be arranged in series, in parallel, or in combination of series and parallel. Preferably, the PFR is used in the transesterification reaction because very high productivity is ensured and the reactants are easily maintained under an optimum reaction condition in the case of using the PFR.

With reference to FIG. 1, there is illustrated a process of producing the bio-diesel oil according to the first aspect of the present invention. In FIG. 1, the PFR is applied to the process of producing the bio-diesel oil, but it is to be understood that modifications to the reactor, for example, use of the batch reactor or the CSTR, will be apparent to those skilled in the art without departing from the spirit of the invention.

As shown in FIG. 1, the oil/fat and alcohol, as the reactants, and alkyl ester as a surfactant are fed into a first mixer 2, and then reacted with each other in the presence of the catalyst in the PFR 3. After the completion of the reaction, glycerine is separated from the resulting product in a separator 4, and alkyl ester is transferred into a first storage tank 5.

At this time, it is preferable that the oil/fat be mixed with alcohol after the oil/fat is preheated in a pre-heater 1 so as to improve the reactivity of the oil/fat with alcohol.

Figure 2:
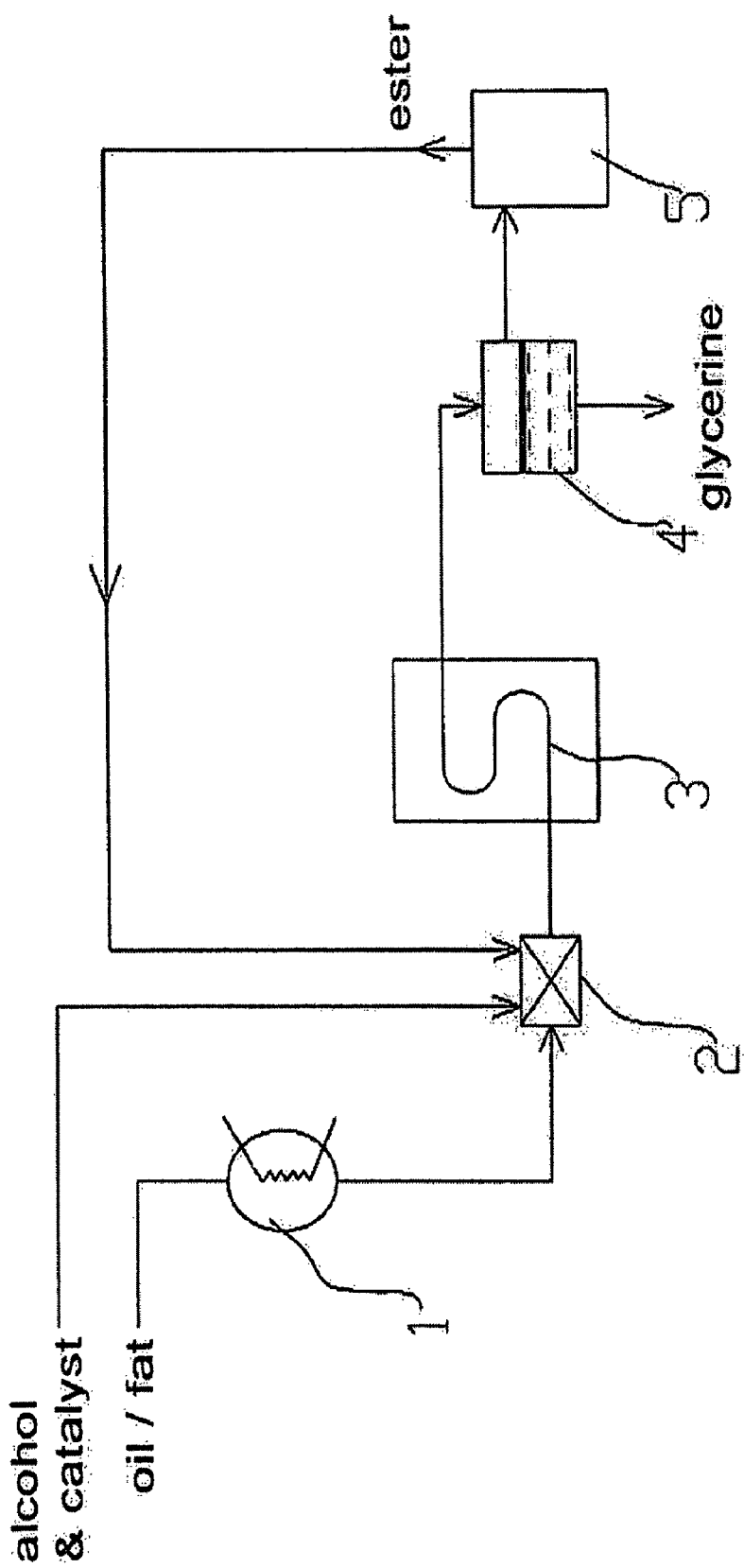
FIG. 2 illustrates the production of a bio-diesel oil using a PFR according to the second aspect of the present invention.

FIG. 2 illustrates a process of producing the bio-diesel oil according to the second aspect of the present invention. Unlike the case of FIG. 1, a portion of alkyl ester is recycled from a second storage tank 5 into a second mixer 2 in FIG. 2. Accordingly, it is not necessary to separately feed alkyl ester into the second mixer 2.

The process as shown in FIG. 2 is very usefully applied to a continuous reaction process using the PFR or CSTR. Additionally, alkyl ester is separately fed from an external feeding source to the reactants in only an early stage of the reaction, and then automatically and continuously recycled to the reactants in a required amount, preferably in the amount of 1 to 30% based on the weight of the oil/fat.

According to the processes of producing the bio-diesel oil in conformity to the first and second aspects of the present invention, the oil/fat is homogeneously mixed with alcohol by use of alkyl ester to increase the reaction rate of the oil/fat with alcohol. Therefore, the plug flow reactor with a relatively short length may be effectively used to produce the bio-diesel oil. Furthermore, it is not necessary to enlarge the scale of the reactor used to produce the bio-diesel oil even though a two-step reaction system is applied to the reactor, and to prolong the length of the plug flow reactor so as to enable a mixture of the oil/fat and alcohol to flow in a turbulent flow.

Even though it is cumbersome and not economical to produce the bio-diesel oil using the batch reactor, because alkyl ester must be repeatedly fed from the external feeding source into the batch reactor, the batch reactor is usefully applied to produce the bio-diesel oil.

After the completion of the transesterification of the oil/fat with alcohol, the catalyst is recovered from the product. In detail, in the case of using the homogeneous catalyst, the resulting product is washed with water to recover the homogeneous catalyst therefrom. On the other hand, in the case of using the heterogeneous solid catalyst, most of the solid catalyst remains in the reactor without a separation process. A small amount of the solid catalyst discharged from the reactor is recovered from the product using a settler or a centrifugal separator. When a mixture of glycerine and alkyl ester produced through the transesterification reaction is left for a predetermined time after the recovery of the catalyst, a boundary layer is formed between glycerine and alkyl ester. At this time, alkyl ester is provided on the boundary layer and glycerine is provided beneath the boundary layer, thereby glycerine and alkyl ester are separated from each other. As described above, after the separation of alkyl ester from glycerine, a portion of alkyl ester may be recycled into the reactants. The resulting alkyl ester may contain a little alcohol. In this respect, the resulting alkyl ester may be subjected to a distillation process to remove alcohol therefrom in order to produce highly pure alkyl ester.

Figure 4A:
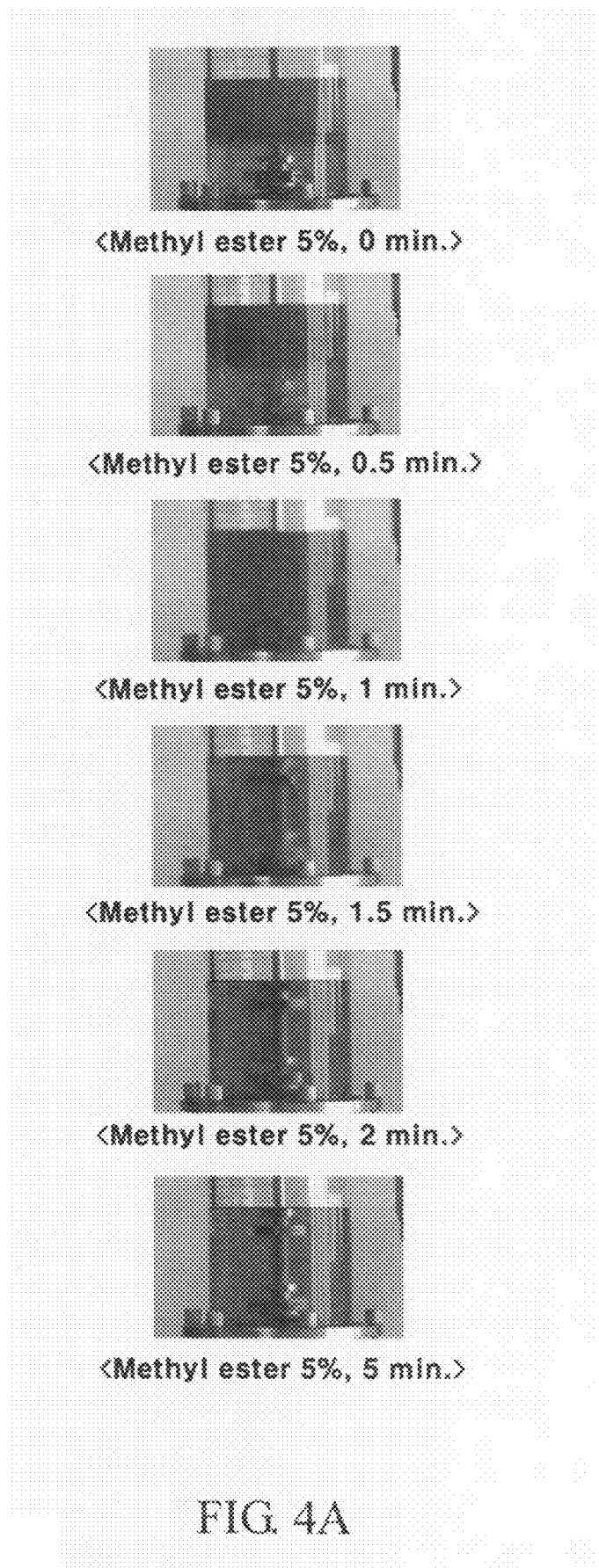
FIG. 4A illustrates pictures showing the variation of a methyl ester plot sample according to a reaction time.
Figure 4B:
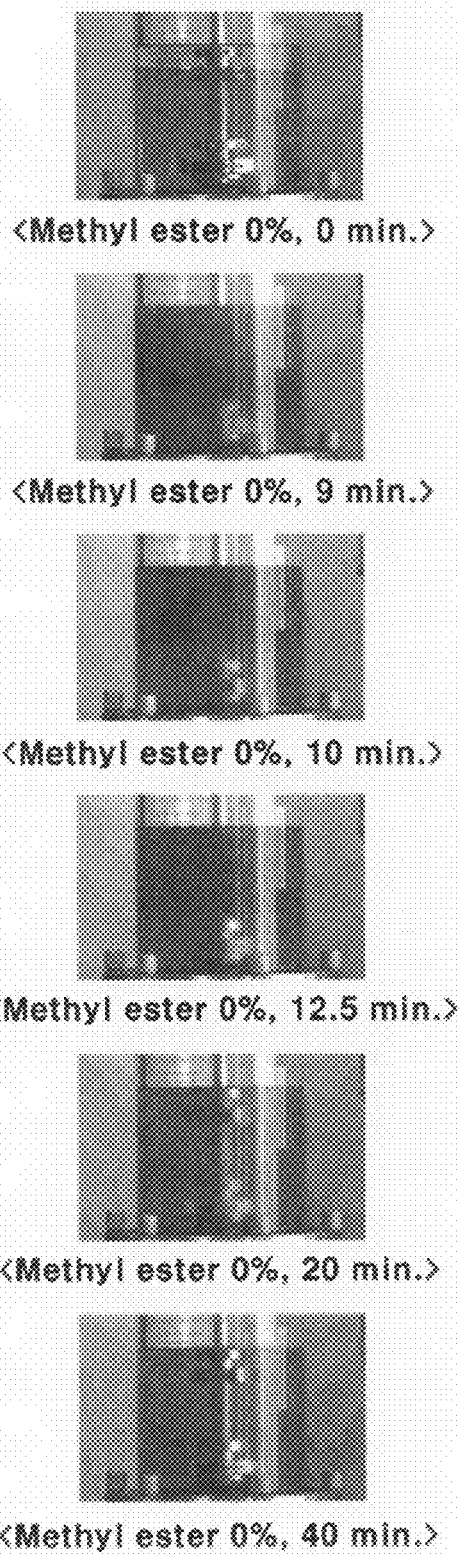
FIG. 4B illustrates pictures showing the variation of a control plot sample according to a reaction time.

FIG. 4A illustrates pictures showing the variation of a methyl ester plot sample according to the reaction time, and FIG. 4B illustrates pictures showing the variation of a control plot sample according to the reaction time.

Referring to FIGS. 4A and 4B, when methyl ester is used in the amount of 5% based on the weight of the oil/fat to produce the bio-diesel oil (FIG. 4A), the transesterification reaction is accomplished in five minutes. On the other hand, in the case of a control plot without using methyl ester (FIG. 4B), the transesterification reaction is accomplished after 40 minutes.

As described above, the basic catalyst used in the transesterification reaction forms a salt from the free fatty acid contained in the oil/fat to undesirably reduce the yield and productivity of the bio-diesel oil.

In an effort to overcome the above disadvantages, there is provided a method of effectively removing the free fatty acid causing the reduction in the yield of the bio-diesel oil and simultaneously converting the free fatty acid into the bio-diesel oil according to the third aspect of the present invention.

A pre-treatment process of the free fatty acid is classified into a process of neutralizing the free fatty acid by adding a basic material to the free fatty acid, and a process of converting the free fatty acid into the bio-diesel oil by adding the acidic catalyst and alcohol to the free fatty acid. At this time, in the case of the former, the free fatty acid is converted into the salt and the salt must be treated as waste. On the other hand, in the case of the latter, the free fatty acid is converted into the bio-diesel oil according to the following Reaction equation 2 to desirably improve the yield of the bio-diesel oil.

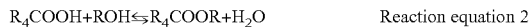

$$R_4COOH + ROH \leftrightarrows R_4COOR + H_2O \quad \text{Reaction equation 2}$$

wherein, R is preferably $C_1$ to $C_{10}$ alkyl groups, and more preferably selected from the group consisting of a methyl group, an ethyl group, a propyl group, a butyl group, a pentyl group, and isomers thereof (structural isomers, stereo-isomers, and the like). $R_4$ is an alkyl group, and preferably the alkyl group in which the number of carbons is properly controlled such that the number of carbons of alkyl ester ($R_4COOR$), as the product obtained according to the Reaction equation 2, is 10 to 24.

As in the case of transesterification, examples of the acidic catalyst used to preesterify the free fatty acid include the liquid sulfuric acid catalyst as the homogeneous catalyst, and the solid acidic catalyst, such as the strong acidic ion exchange resin and sulfate zirconia, as the heterogeneous catalyst. The solid acidic catalyst is useful to pre-esterify the free fatty acid in that it can be regenerated and scarcely generates wastewater. However, in the case of using the solid acidic catalyst, the solid acidic catalyst does not smoothly come into contact with the reactants in comparison with the liquid sulfuric acid catalyst. In this respect, the insufficient contact between the solid acidic catalyst and the reactants obstructs the non-polar oil/fat contained in a major portion in the reactants from coming into contact with the free fatty acid, alcohol and the catalyst to reduce the reaction rate.

The insufficient contact between the solid acidic catalyst and the reactants may be overcome by adding alkyl ester to the reactants. In other words, when alkyl ester is added to the pre-esterification process of the free fatty acid, a contact efficiency between the free fatty acid, alcohol and the catalyst is improved to enable the free fatty acid to be easily converted into the bio-diesel oil. The resulting alkyl ester acting as the bio-diesel oil thus converted contributes to improving the contact efficiency between the oil/fat and alcohol in the transesterification reaction.

At this time, the amount of alkyl ester used in the pre-esterification process of the free fatty acid is preferably 1 to 30% based on the weight of the feed oil/fat containing the free fatty acid.

It is preferable that the acidic catalyst be applied to the pre-esterification process of the free fatty acid in a minimum amount as long as the acidic catalyst sufficiently esterifies the free fatty acid. In this respect, the liquid acidic catalyst and the solid acidic catalyst are applied to the pre-esterification process of the free fatty acid in different amounts. Preferably, the amount of the liquid acidic catalyst as the homogeneous catalyst is 0.2 to 3% based on the weight of the feed oil/fat, and the amount of the solid acidic catalyst as the heterogeneous catalyst is 5 to 80% based on the volume of a packed bed reactor used in the pre-esterification reaction. Additionally, in the case of using the batch reactor or the continuous stirred tank reactor, it is preferable that the amount of the solid acidic catalyst be relatively low 5 to 40% in consideration of the agitation characteristics and physical properties of the solid acidic catalyst.

A reaction condition of the pre-esterification process of the free fatty acid is not specifically limited, but it is preferable that the pre-esterification process be conducted at 40 to 120° C. for 0.05 to 3 hours according to the kind of reactant.

Figure 3:
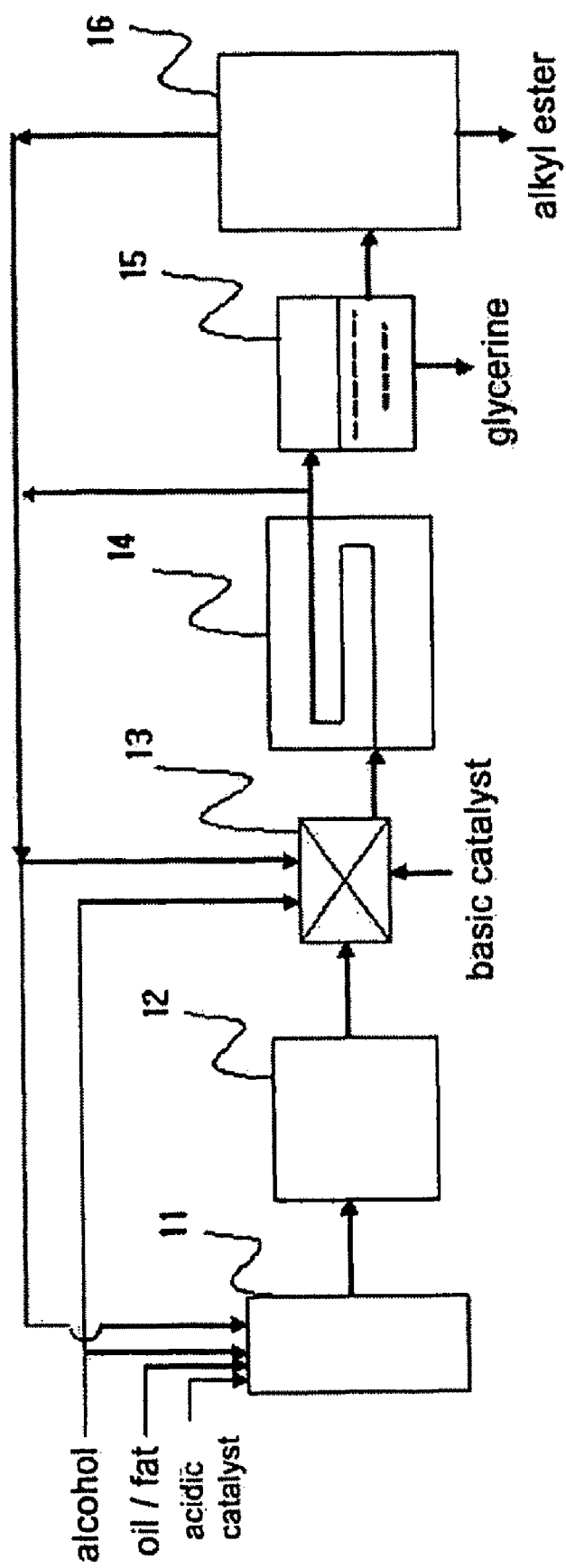
FIG. 3 illustrates the production of a bio-diesel oil through a pre-esterification process and a transesterification process using a PFR according to the third aspect of the present invention.

Referring to FIG. 3, there is illustrated a system of producing the bio-diesel oil according to the third aspect of the present invention. The system includes a reactor 11, an evaporator 12, a mixer 13, a plug flow reactor 14, a separator 15, and a storage tank 16.

A detailed description will be given of the production of the bio-diesel oil according to the third aspect of the present invention, referring to FIG. 3. The oil/fat, alcohol, and the acidic catalyst are fed into the reactor 11, and a predetermined amount of alkyl ester is then added into the reactor 11 to esterify the free fatty acid contained in the oil/fat. The resulting mixture of the oil/fat and alkyl ester obtained from the reactor 11 is transferred to the evaporator 11 to remove moisture therefrom. The oil/fat, alcohol, and alkyl ester subjected to the pre-esterification process are fed into the mixer 13 and then reacted with each other in the presence of a catalyst in the plug flow reactor 14. After the completion of the reaction, glycerine is separated from the resulting product in the separator 15, and alkyl ester is transferred to the storage tank 16.

At this time, a portion of alkyl ester is preferably recycled from the storage tank 16 to the mixer 13 and the reactor 11, therefore it is feasible to avoid the cumbersome problem that alkyl ester is fed from an external feeding source into the mixer 13 and the reactor 11.

A better understanding of the present invention may be obtained through the following examples which are set forth to illustrate, but are not to be construed as the limit of the present invention.

MODE FOR INVENTION

EXAMPLE 1

(1) Methyl Ester (ME) Plot 1450 g of refined soybean oil(SBO) was fed into a batch reactor and preheated at 75° C. for 30 min. After the completion of the preheating of the refined soybean oil, 212.8 g of methanol, 1% of potassium hydroxide (17.0 g, 85% assay KOH) based on the weight of the refined soybean oil, and 5% of methyl ester based on the weight of the refined soybean oil were added into the batch reactor, and then agitated at an agitation speed of 80 rpm. The reaction was completed after 5 min since the reactants started to be agitated. The degree of the reaction was observed according to the reaction time, and the results are shown in FIG. 4A.

(2) Control Plot 1450 g of refined soybean oil was fed into a batch reactor and preheated at 75° C. for 30 min. After the completion of the preheating of the refined soybean oil, 212.8 g of methanol, and 1% of potassium hydroxide (17.0 g, 85% assay KOH) based on the weight of the refined soybean oil were added into the batch reactor, and then agitated at a relatively low agitation speed of 80 rpm. The reaction was completed after 40 min since the reactants started to be agitated. The degree of the reaction was observed according to the reaction time, and the results are shown in FIG. 4B.

As shown in FIG. 4A, when 5% of methyl ester based on the weight of the refined soybean oil was added into the batch reactor, a boundary layer between the soybean oil and methanol disappeared in one minute since the boundary layer started to be formed, thereby the soybean oil and methanol were homogeneously mixed with each other to complete the reaction in five minutes.

On the other hand, in the case of the control plot, the soybean oil was immiscible with methanol because their polarities were different from each other, and methanol existed in an upper phase while the soybean oil in a lower phase. At this time, the phase separation between methanol and the soybean oil was maintained for 10 min. Even though a mixture of methanol and the soybean oil was continuously agitated to remove the phase separation, the reaction was neither smoothly conducted nor completed after 30 min since the phase separation between methanol and the soybean oil started to disappear (refer to FIG. 4B).

Figure 5:
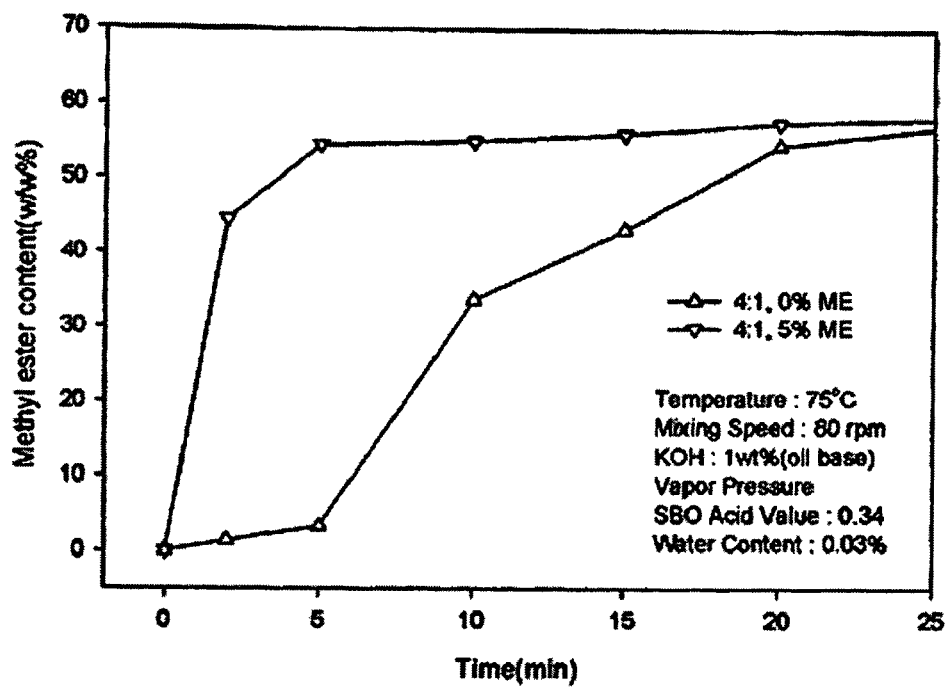
FIG. 5 is a graph showing a methyl ester yield as a function of a reaction time for methyl ester and control plots according to example 1 of the present invention.

Meanwhile, in the cases of the methyl ester plot and the control plot, yields of methyl ester were measured after 25 min, and the results are shown in FIG. 5. As shown in FIG. 5, the methyl ester plot produced much more methyl ester than the control plot after five minutes since the reactants started to react with each other. Accordingly, in the case of the methyl ester plot, a bio-diesel oil was produced in a relatively short time in a more amount than the case of the control plot.

In the example 1, the bio-diesel oil was produced using the batch reactor. However, it will be more easily understood by those skilled in the art that because the batch reactor and a PFR have the same reaction kinetics as each other, the same results as in the example 1 are obtained when the procedure according to the example 1 is applied to the PFR.

EXAMPLE 2

(1) 5% Methyl Ester (ME) Plot 200 g of refined soybean oil, 29.4 g of methanol (a molar ratio of methanol and the refined soybean oil is 4:1), 1% of potassium hydroxide based on the weight of the refined soybean oil, and 5% of methyl ester based on the weight of the refined soybean oil were fed into a batch reactor, and then reacted with each other at 80° C. while being agitated at an agitation speed of 50 rpm for 30 min to produce methyl ester as a bio-diesel oil.

(2) 20% Methyl Ester (ME) Plot 200 g of refined soybean oil, 29.4 g of methanol (a molar ratio of methanol and the refined soybean oil is 4:1), 1% of potassium hydroxide based on the weight of the refined soybean oil, and 20% of methyl ester based on the weight of the refined soybean oil were fed into a batch reactor, and then reacted with each other at 80° C. while being agitated at an agitation speed of 50 rpm for 30 min to produce methyl ester as a bio-diesel oil.

(3) Control Plot 200 g of refined soybean oil, 29.4 g of methanol (a molar ratio of methanol and the refined soybean oil is 4:1), and 1% of potassium hydroxide based on the weight of the refined soybean oil were fed into a batch reactor, and then reacted with each other at 80° C. while being agitated at an agitation speed of 50 rpm for 30 min to produce methyl ester.

Figure 6:
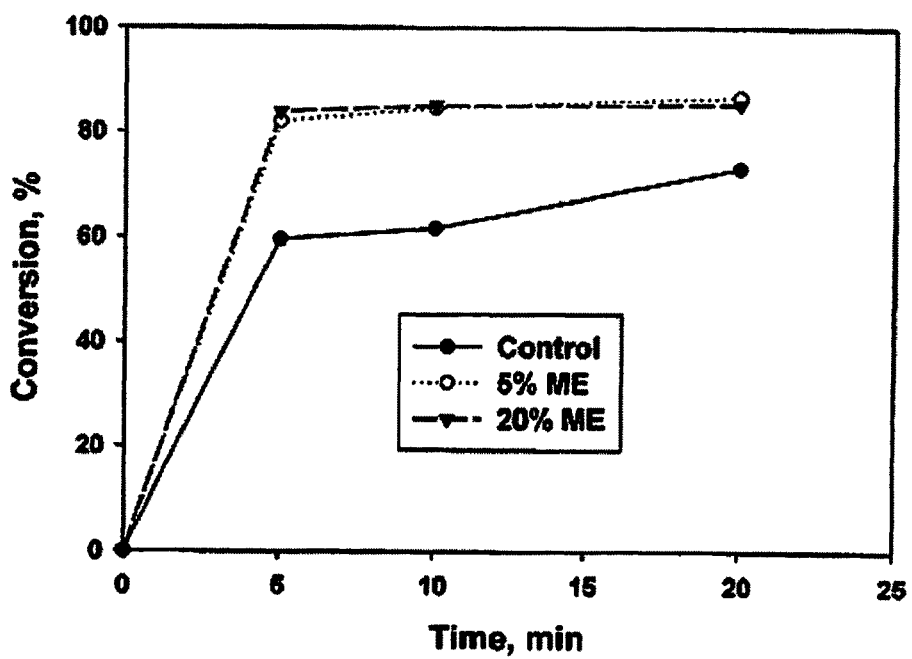
FIG. 6 is a graph showing a methyl ester yield as a function of a reaction time for methyl ester and control plots according to example 2 of the present invention.

FIG. 6 is a graph showing a yield of methyl ester as a function of a reaction time for the 5% methyl ester plot, 20% methyl ester plot, and the control plot.

As shown in FIG. 6, in the cases of the 5% methyl ester plot and the 20% methyl ester plot, a yield of methyl ester of 80% or more was obtained in five minutes since the reactants started to be agitated. On the other hand, in the case of the control plot without the use of methyl ester, the yield of methyl ester did not approach 80% even after a reaction time of 20 min.

EXAMPLE 3

(1) Methyl Ester Plot (0% ME, 5% ME)

1450 g of refined soybean oil was fed into a reactor and preheated at 75° C. for 30 min. After the completion of the preheating of the refined soybean oil, 212.8 g of methanol (a molar ratio of methanol and the refined soybean oil is 4:1), 1% of potassium hydroxide (85% assay KOH) based on the weight of the refined soybean oil, 0% of methyl ester based on the weight of the refined soybean oil, and 5% of methyl ester based on the weight of the refined soybean oil were added into the reactor, and then agitated at an agitation speed of 80 rpm for 25 min to produce methyl ester as a product.

(2) Control Plot 1450 g of refined soybean oil was fed into a reactor and preheated at 75° C. for 30 min. After the completion of the preheating of the refined soybean oil, 212.8 g of methanol, and 1% of potassium hydroxide (85% assay KOH) based on the weight of the refined soybean oil were added into the reactor, and then agitated at an agitation speed of 80 rpm for 25 min to produce methyl ester as a product.

Figure 7:
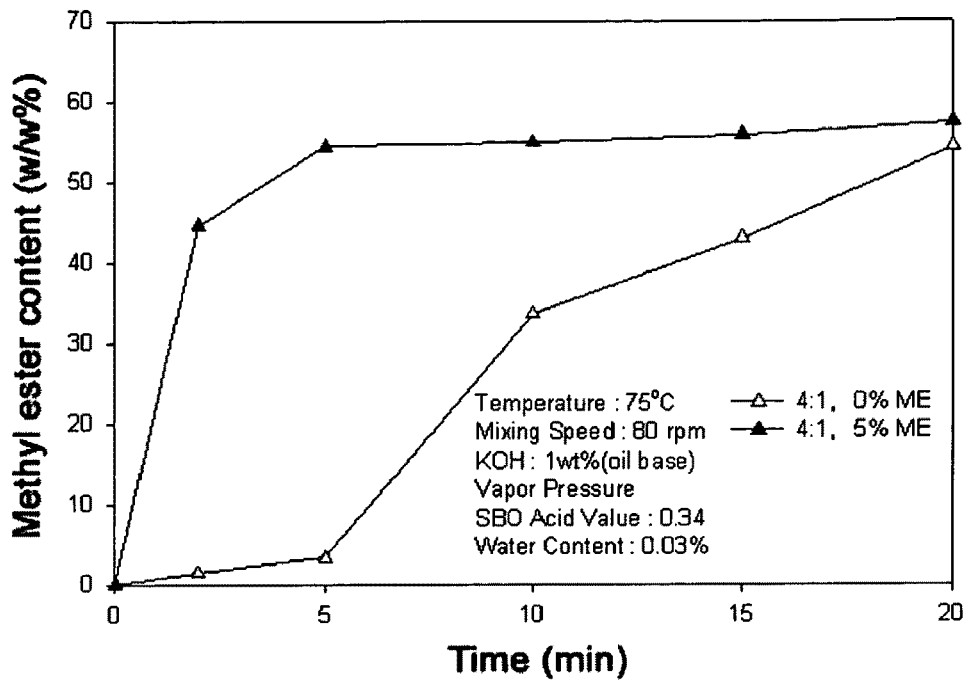
FIG. 7 is a graph showing a methyl ester yield as a function of a reaction time for methyl ester and control plots according to example 3 of the present invention.

FIG. 7 is a graph showing a yield of methyl ester as a function of a reaction time for the methyl ester plots and the control plot.

As shown in FIG. 7, initial reaction rates (methyl ester content/reaction time) of the methyl ester plots are faster than the initial reaction rate of the control plot. Accordingly, it can be seen that the methyl ester plots produce a bio-diesel oil in a relatively large amount in a relatively short time in comparison with the control plot.

EXAMPLE 4

(1) Control Plot 200 g of refined soybean oil containing 5% of an oleic acid as a free fatty acid, 17.6 g of methanol, and 40 g of a strong acidic ion exchange resin (Amberyst-15 manufactured by Rohm & Haas Inc., USA) as a catalyst were fed into a reactor, and then reacted with each other at 80° C. while being agitated at an agitation speed of 200 rpm for 60 min to convert the free fatty acid into fatty acid methyl ester (FAME) acting as a bio-diesel oil.

(2) Methyl Ester Plot

The procedure of the control plot was repeated to produce methyl ester acting as a bio-diesel oil, except that 10% and 20% of methyl ester based on the weight of the refined soybean oil were added into a reactor.

Figure 8:
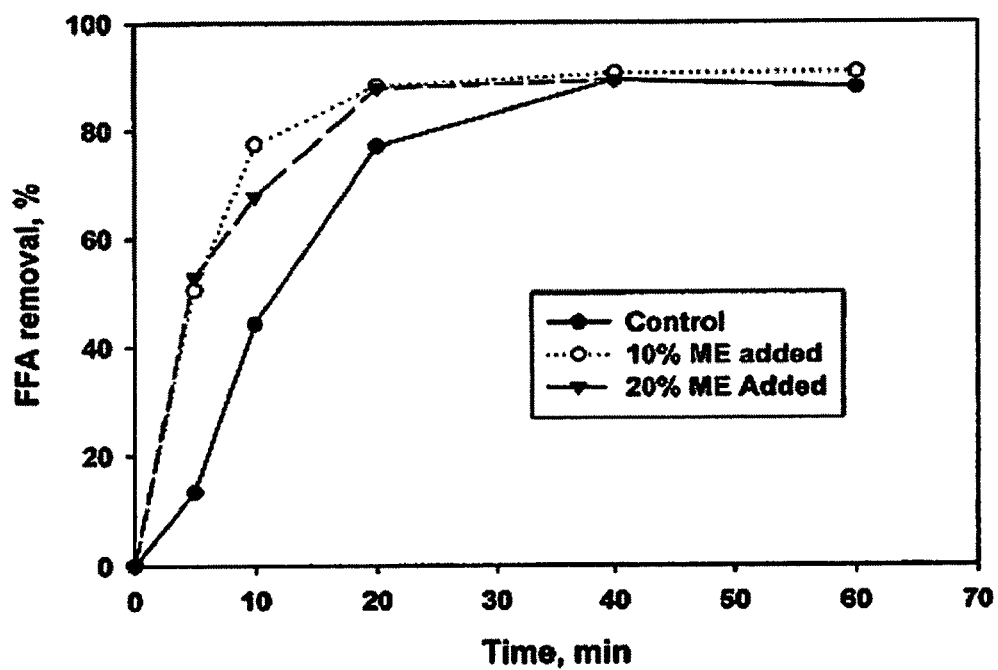
FIG. 8 is a graph showing a free fatty acid (FFA) conversion as a function of a reaction time for methyl ester and control plots subjected to a pre-esterification process according to example 4 of the present invention.

FIG. 8 is a graph showing a free fatty acid conversion as a function of a reaction time for the control plot and the methyl ester plots, in which the removal of the oleic acid due to an esterification reaction of the oleic acid with methanol in the presence of an acidic catalyst is estimated as an index of the production of methyl ester.

As shown in FIG. 8, the 10% and 20% methyl ester plots ensure better reaction efficiency than the control plot.

EXAMPLE 5

(1) Control Plot 200 g of waste palm oil containing 6% of a free fatty acid, discharged from a factory producing Ramen noodles, 17.6 g of methanol, and 40 g of an Amberlyst-15 catalyst were fed into a reactor, and then were agitated at 80° C. at an agitation speed of 200 rpm for 60 min to produce methyl ester. At this time, the waste palm oil was filtered several times to remove floating matters, except for liquid components therefrom, before it was fed into the reactor.

(2) Methyl Ester Plot

The procedure of the control plot was repeated to produce methyl ester acting as a bio-diesel oil, except that 10% and 20% of methyl ester based on the weight of the waste palm oil were added into a reactor.

Figure 9:
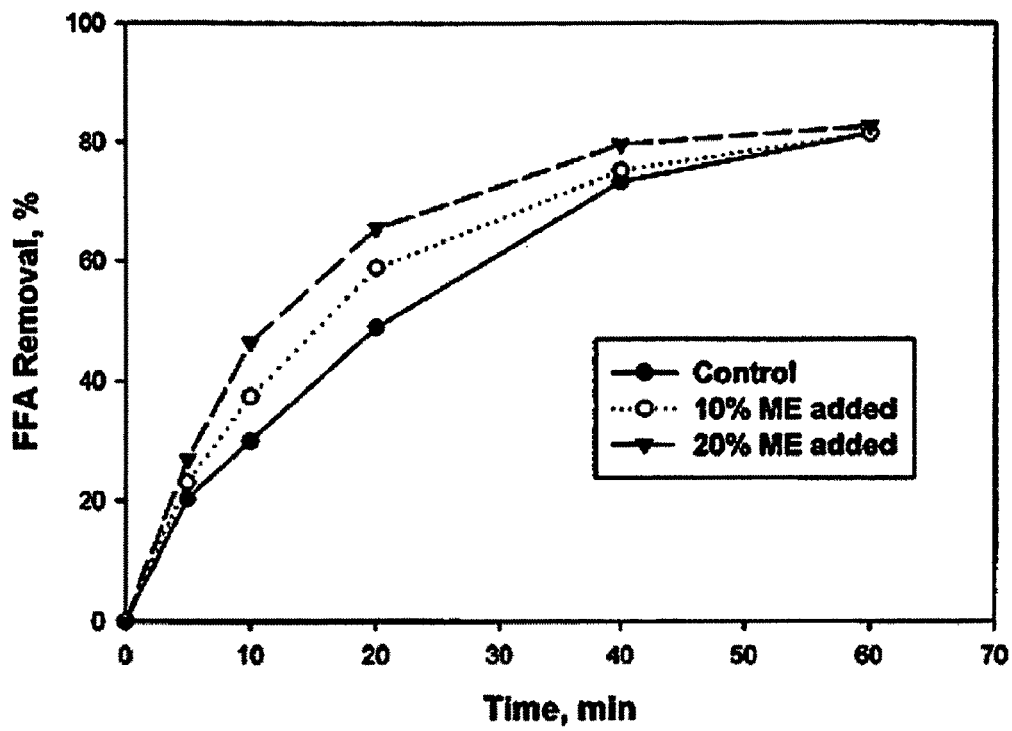
FIG. 9 is a graph showing a free fatty acid conversion as a function of a reaction time for methyl ester and control plots subjected to a pre-esterification process according to example 5 of the present invention.

FIG. 9 is a graph showing a free fatty acid conversion as a function of a reaction time for the control plot and the methyl ester plots, in which the removal of the free fatty acid due to an esterification reaction of the free fatty acid with methanol in the presence of an acid catalyst is estimated as an index of the production of methyl ester.

As shown in FIG. 9, the 10% and 20% methyl ester plots ensure better reaction efficiency than the control plot. In the case of the example 4, the oleic acid acting as the free fatty acid was mixed with the refined soybean oil. On the other hand, in the case of the example 5, removal efficiency of the free fatty acid was high even though the waste palm oil having a high free fatty acid content was used to produce methyl ester.

EXAMPLE 6

(1) Methyl Ester Plot 1450 g of degummed crude rapeseed oil(RSO), 212.8 g of methanol (a molar ratio of methanol and degummed crude rapeseed oil is 4:1), 1% of potassium hydroxide (85% assay KOH) based on the weight of the degummed crude rapeseed oil, 10% and 20% of methyl ester based on the weight of the degummed crude rapeseed oil were fed into a reactor.

The resulting mixture was agitated at 75° C. under pressure of 2.0 kg/cm² (air gauge pressure) at an agitation speed of 50 rpm for 40 min to produce methyl ester acting as a bio-diesel oil.

(2) Control Plot 1450 g of degummed crude rapeseed oil, 212.8 g of methanol (a molar ratio of methanol and degummed crude rapeseed oil is 4:1), and 1% of potassium hydroxide (85% assay KOH) based on the weight of the degummed crude rapeseed oil were fed into a reactor, and then agitated at 75° C. under pressure of 2.0 kg/cm² (air gauge pressure) at an agitation speed of 50 rpm for 40 min to produce methyl ester acting as a bio-diesel oil.

Figure 10:
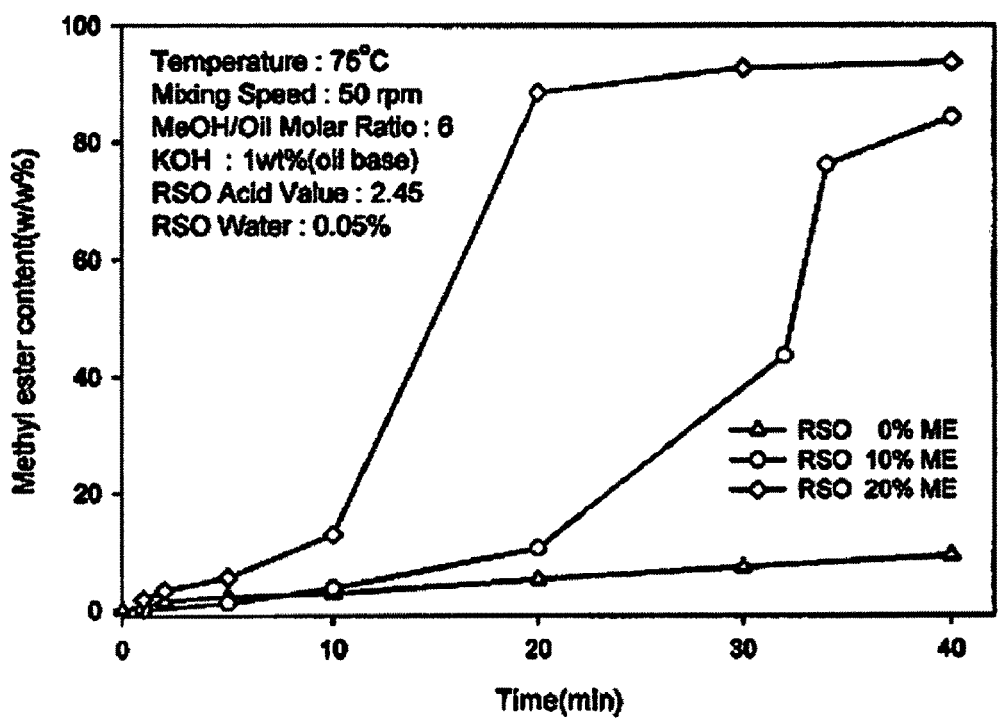
FIG. 10 is a graph showing a methyl ester yield as a function of a reaction time for methyl ester and control plots according to example 6 of the present invention (RSO: rapeseed oil).

FIG. 10 is a graph showing a yield of methyl ester as a function of a reaction time for the methyl ester plot and the control plot. As shown in FIG. 10, the 10% and 20% methyl ester plots ensure the better yield of methyl ester and reaction rate than the control plot even though the reactants were agitated at the relatively slow agitation speed of 50 rpm.

INDUSTRIAL APPLICABILITY

As described above, the present invention provides a method of producing a bio-diesel oil in a desired amount in a relatively short time, in which reactants are homogeneously mixed with each other to form a single liquid phase when oil/fat and alcohol are subjected to a transesterification reaction in the presence of alkyl ester.

In the examples of the present invention, the bio-diesel oil is produced using a batch reactor, but because the batch reactor and a PFR have the same reaction kinetics as each other, use of the PFR gives rise to the same results as use of the batch reactor according to the example 1. In other words, when alkyl ester is added to the reactants, like the examples of the present invention, to produce the bio-diesel oil using the PFR, the reactants are homogeneously mixed with each other to form the single liquid phase in order to rapidly increase the reaction rate to largely reduce a length of the PFR, thereby reducing the size of the space required to produce the bio-diesel oil and ensuring economic efficiency. The improvement in the reaction rate as described above is accomplished by adding alkyl ester to the reactants to homogeneously mix the reactants to overcome a chemical property difference, such as a polarity difference, between the reactants. Therefore, the method of producing the bio-diesel oil according to the present invention can be applied to agitation and non-agitation reaction systems, homogeneous-based and heterogeneous-based catalytic reaction systems using physical property differences of catalysts, and acidic and basic catalytic systems.

Meanwhile, when alkyl ester acting as the product is recycled to the reactants after the reaction of oil/fat with alcohol, a relatively high reaction rate is continuously maintained to improve the productivity and yield of the bio-diesel oil.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of producing a bio-diesel oil, comprising:
  (a) pre-esterifying a free fatty acid, contained in oil/fat, with an alcohol in the presence of an acidic catalyst to create a reaction mixture comprising an alkyl ester; and
  (b) transesterifying the reaction mixture to create a product comprising the alkyl ester,
  wherein a portion of the product comprising the alkyl ester produced by the step (b) is directly recycled to the reaction mixture of step (a) and/or step (b) prior to separating the alkyl ester and glycerine in a separator.

2. The method as set forth in claim 1, wherein the step (a) further comprises adding alkyl ester as a product to the reactants.

3. The method as set forth in claim 1 or 2, wherein the alkyl ester of the step (a) or/and the step (b) is added to the reactants in an amount of 1 to 30% based on a weight of the oil/fat.

4. The method as set forth in claim 1, wherein the oil/fat of the step (a) is selected from the group consisting of vegetable oil/fat, animal oil/fat, waste frying oil, and regenerated oil/fat, containing the free fatty acid.

5. The method as set forth in claim 1, wherein the alcohol of the step (a) and the step (b) is selected from the group consisting of C1 to C10 alcohols, and a mixture thereof.

6. The method as set forth in claim 1, wherein the oil/fat containing the free fatty acid reacts with the alcohol in a molar ratio of 1:0.3 to 1:3 in the step (a), and the oil/fat reacts with the alcohol in a molar ratio of 1:3 to 1:12 in the step (b).

7. The method as set forth in claim 1, wherein the step (b) is conducted in a presence of a basic catalyst or the acidic catalyst.

8. The method as set forth in claim 7, wherein the basic catalyst or acidic catalyst is a homogeneous catalyst, and is added to reactants in an amount of 0.3 to 2.0% based on a weight of oil/fat.

9. The method as set forth in claim 7, wherein the basic catalyst or acidic catalyst is a heterogeneous catalyst, and is added to reactants in an amount of 5 to 80% based on a volume of a reactor.

10. The method as set forth in claim 1, wherein the step (a) and the step (b) are conducted in a batch reactor, a plug flow reactor, or a continuous stirred tank reactor, and when a plurality of reactors are used to conduct the step (a) and the step (b), the reactors are arranged in series, in parallel, or in combination of series and parallel.

* * * * *